(12) United States Patent
Abe et al.

(10) Patent No.: US 6,829,051 B2
(45) Date of Patent: Dec. 7, 2004

(54) OPTICAL APPARATUS

(75) Inventors: Katsuyuki Abe, Hachioji (JP); Kazuhiko Osa, Hachioji (JP)

(73) Assignee: Olympus Corporation, Tokyo (JP)

( * ) Notice: Subject to any disclaimer, the term of this patent is extended or adjusted under 35 U.S.C. 154(b) by 164 days.

(21) Appl. No.: 10/189,622

(22) Filed: Jul. 8, 2002

(65) Prior Publication Data
US 2003/0011772 A1 Jan. 16, 2003

(30) Foreign Application Priority Data
Jul. 10, 2001 (JP) ........................................ 2001-209119

(51) Int. Cl.[7] .............................................. G01N 21/64
(52) U.S. Cl. ................................... 356/417; 250/458.1
(58) Field of Search ................................ 356/317, 318, 356/419, 417; 250/458.1, 459.1, 461.1, 461.2; 359/385, 388

(56) References Cited
FOREIGN PATENT DOCUMENTS

| JP | Hei8-320437 | 12/1996 |
| JP | Hei11-052252 | 2/1999 |
| JP | Hei11-223773 | 8/1999 |

Primary Examiner—F. L. Evans
(74) Attorney, Agent, or Firm—Kenyon & Kenyon

(57) ABSTRACT

An optical apparatus including an illuminating optical system for illuminating a sample with light from a light source, a first wavelength selecting member, a light beam splitter for directing illuminating light toward the sample, an objective lens, a detector, and a second wavelength selecting member disposed between the objective lens and the detector, in which the first wavelength selecting member has a wavelength selecting element for selectively transmitting light having wavelengths in a predetermined region out of the illuminating light, the second wavelength selecting member has a wavelength selecting element for transmitting light having a predetermined wavelength out of light reflected by the sample, and the light beam splitter has an optical element having transmittance not lower than 85% and reflectance not higher than 14% in a wavelength region not shorter than 400 nm and not longer than 700 nm. The optical apparatus permits observing fluorescent light at the same time with a high efficiency.

23 Claims, 15 Drawing Sheets

OPTICAL APPARATUS

BACKGROUND OF THE INVENTION a) Field of the Invention

The present invention relates to an optical apparatus for irradiating a sample with light and detecting light, fluorescent light in particular, emitted from the sample. Furthermore, the present invention relates to an optical apparatus which is capable of detecting fluorescent light having a plurality of wavelengths at the same time.

b) Description of the Prior Art

For biological researches in the recent years, functions of living bodies have been studied using not fixed samples but living samples. Speaking concretely of the biological researches, functions of protein molecules are clarified by attaching the protein molecules which attract attentions to fluorescent molecules which attach specifically to the protein molecules, and observing and analyzing movements and distributions of the molecules using fluorescence microscopes. In addition, fluorescent substances which have recently appeared make it possible to allow light emitting proteins to exist in cells, thereby observing and analyzing proteins and the like in conditions where physiological activities are kept better. Furthermore, attempts are being made to measure movements and distributions of a plurality of molecules at the same time using a plurality of fluorescent dyes for clarifying higher functions in cells.

Described in Cell Engineering (Vol. 17, No. 6, pp956 to 965) is an apparatus which is configured to irradiate cells with excitation light at intensities as low as possible, thereby lessening damages on cells in order to make it possible to observe the cells in living conditions.

The apparatus described in this literature uses a light attenuating filter (ND filter) which is disposed in an illuminating optical system for weakening the excitation light.

Importance of the ND filter in observation of such fluorescent substances and a density of the ND filter appropriate for observing living cells are described in "GFP and Bio Imaging" (separate volume of Experimental Medicine, Experiment Course in Post Genome Age 3, 2000, p156 issued by Youdo, Japan).

Furthermore, observing apparatuses which are used for observations with a plurality of fluorescent dyes are disclosed by Japanese Patents Kokai Publication No. Hei 8-320437, No. Hei 11-52252 and No. Hei 11-223773.

The apparatus disclosed by Japanese Patent Kokai Publication No. Hei 8-320437 uses a dichroic mirror for multiple excitation such as triple excitation or quadruple excitation as a dichroic mirror for observing a plurality of fluorescent light at the same time. There is available a dichroic mirror which has a spectral characteristic shown in FIG. 19. This dichroic mirror is manufactured by a method which deposits a thin film which is referred to as the so-called soft coat film while maintaining a substrate in the vicinity of normal temperature in order to obtain the dichroic mirror having the spectral characteristic shown in FIG. 19. Since this soft coat film has low resistance to temperature and humidity variations, chemicals and physical impacts such as that caused by wiping at a surface cleaning time, the spectral characteristic of the soft coat film is often deteriorated with time lapse and the soft coat film requires a remarkably high cost for maintenance.

Furthermore, a technique for observing samples multiply dyed with fluorescent dyes is described in a published bulletin of Japanese Patent Kokai Publication No. Hei 11-52252. However, the technique described in this bulletin is configured to allow independent dichroic mirrors suited to the fluorescent dyes to be used in exchange without using a dichroic mirror for multiple excitation. Accordingly, this technique does not permit observing movements and distributions of a plurality of molecules using a plurality of fluorescent dyes at the same time. Furthermore, an observing apparatus for observation by this technique allows vibrations to be produced when the dichroic mirrors are exchanged at a high speed since the apparatus uses a dichroic mirror holding member which is more complicated and larger than an excitation filter and as absorption filter. Furthermore, the apparatus requires preparing the dichroic mirrors in a number of the fluorescent dyes for observing the plurality of fluorescent dyes at the same time, thereby posing a problem of cost. Furthermore, differences among parallelisms of the dichroic mirrors produce deviations among observed fluorescent images. Means for canceling the deviations which is described in this bulletin is extremely complicated and it is difficult to cancel the deviations by simple and inexpensive means.

Furthermore, Japanese Patent Kokai Publication No. Hei 11-223773 discloses a technique which is configured to permit observing a plurality of fluorescent images at the same time using a plurality of dichroic mirrors disposed in directions of optical axes of an objective lens and an observing optical system, but this technique requires a plurality of light sources.

SUMMARY OF THE INVENTION

The present invention has been achieved in circumstances described above and has an object to provide as optical apparatus which is configured to permit simultaneously observing a plurality of fluorescent dyes used for clarifying functions of living bodies.

In order to accomplish the above described object, an optical apparatus according to the present invention comprises a light source, an illuminating optical system for illuminating a sample with illuminating light from the light source, a first wavelength selecting member disposed after the illuminating optical system, a light beam splitter for directing the illuminating light from the light source to the sample, an objective lens disposed between the light beam splitter and the sample, a detector for detecting light from the sample through the objective lens and a second wavelength selecting member disposed in the objective lens system or between the objective lens and the detector, the first wavelength selecting member has at least a wavelength selecting element which selectively transmits light having wavelengths in a predetermined region, the second wavelength selecting member has at least another second wavelength selecting element which transmits light having a predetermined wavelength out of light reflected by the sample or emitted from the sample, and the light beam splitter has an optical element which has a transmitting-reflecting characteristic of transmittance not lower than 85% and reflectance not higher than 15% at least in a wavelength region from 400 nm to 700 nm.

An optical apparatus according to the present invention has a configuration like that described above, in which an optical element of a light beam splitter has a shape of a plane parallel plate and an antireflection coating at least on a surface (second surface) located on a side opposite to a surface (first surface) on which illuminating light are incident from a light source.

In the optical apparatus according to the present invention, the optical element of the light beam splitter may have the antireflection coatings on both the first surface and the second surface.

Furthermore, an optical apparatus according to the present invention is configured to have either of the configurations described above, use a light beam splitter which further comprises a dichroic mirror and allow the optical element to be switched to the dichroic mirror.

DETAILED DESCRIPTION OF THE PREFERRED EMBODIMENTS

Figure 1:
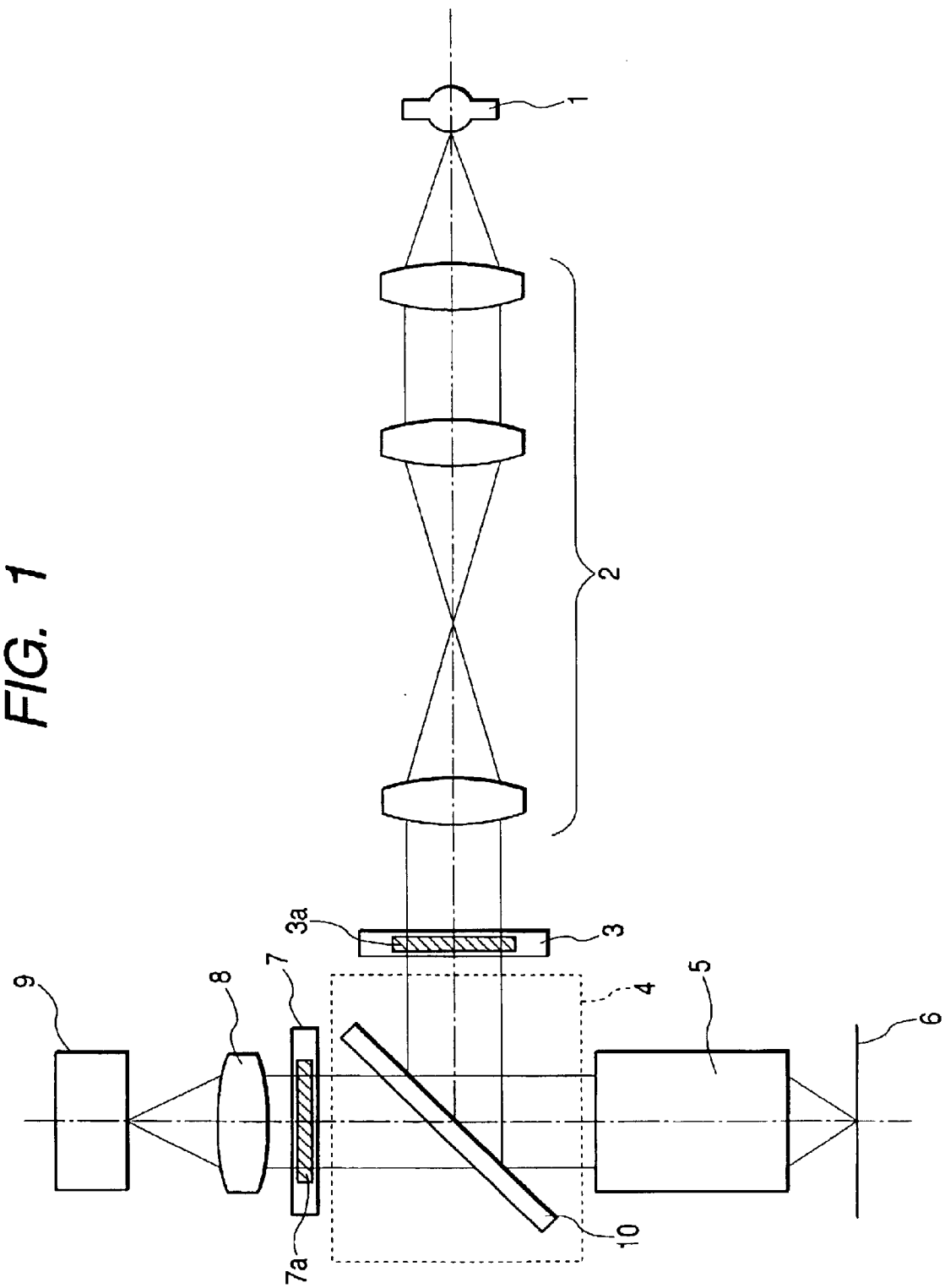
FIG. 1 is a diagram showing a configuration of an optical apparatus according to a first embodiment of the present invention.

A first embodiment of the present invention is configured as shown in FIG. 1. The first embodiment has a basic configuration of an erecting type microscope, and in FIG. 1, a reference numeral 1 represents a light source, a reference numeral 2 designates an illuminating optical system, a reference numeral 3 denotes a first wavelength selecting member having a first wavelength selecting element 3a, a reference numeral 4 represents a light beam splitter having an optical element 10, a reference numeral 5 designates an objective lens, a reference numeral 6 denotes a sample, a reference numeral 7 represents a second wavelength selecting member having a second wavelength selecting element 7a, a reference numeral 8 designates an imaging lens (tube lens) and a reference numeral 9 denote a detector. Furthermore, a mercury lamp, for example, is used as the light source 1 among the above described components.

Light emitted from the light source 1 which is a mercury lamp include light ranging from ultraviolet light through visible light to near infrared light, transmit through the illuminating optical system 2 and are incident on the first wavelength selecting member 3. Disposed in this first wavelength selecting member 3 is a first optical filter 3a having a predetermined wavelength as the first wavelength selecting element. The filter 3a disposed in the first wavelength selecting member 3 is positioned in an optical path to transmit light having wavelengths only within a predetermined region out of light within a range from the ultraviolet region to the visible region. Light which has transmitted through the filter 3a is incident on the light beam splitter 4. The optical element 10 which is disposed in the light beam splitter 4 is positioned so as to have an angle of 45° relative to an optical axis of the illuminating optical system 2. Accordingly, excitation light which is incident on the light beam splitter 4 are reflected toward the objective lens 5. The light which has been reflected by the optical element 10 and emerged from the light beam splitter 4 illuminates the sample 6 by way of the objective lens 5.

The sample 6 which is illuminated with the excitation light as described above emits fluorescent light. That is, the excitation light reflected by the sample and the fluorescent light are produced. The fluorescent light and the excitation light pass through the objective lens 5, and are incident onto the light beam splitter 4. The light incident on the light beam splitter 4 transmit through the optical element 10 and are incident on the second wavelength selecting member 7.

Figure 2:
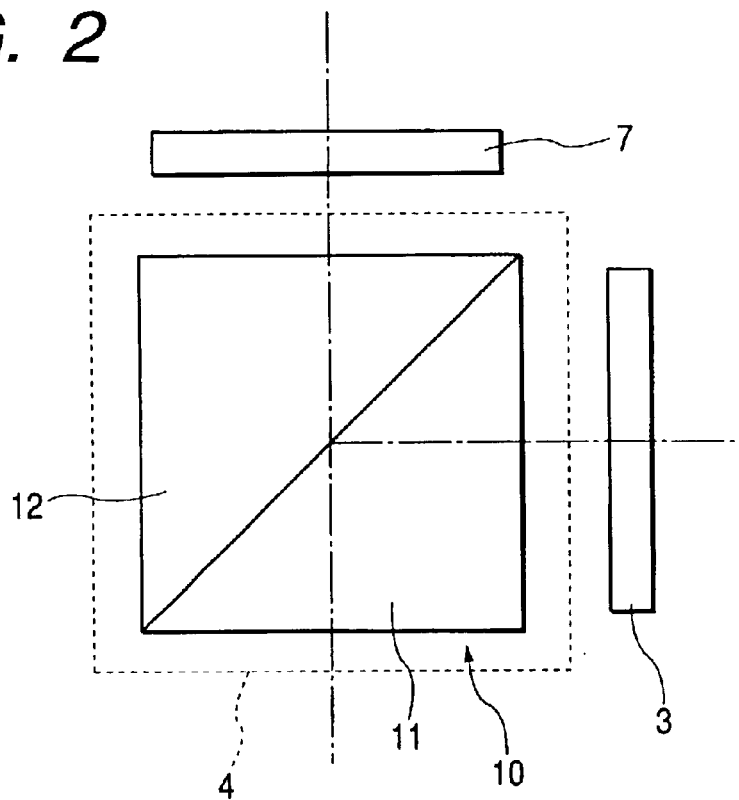
FIG. 2 is a diagram showing another example of a light beam splitter to be used in the optical apparatus according to the present invention.
Figure 3:
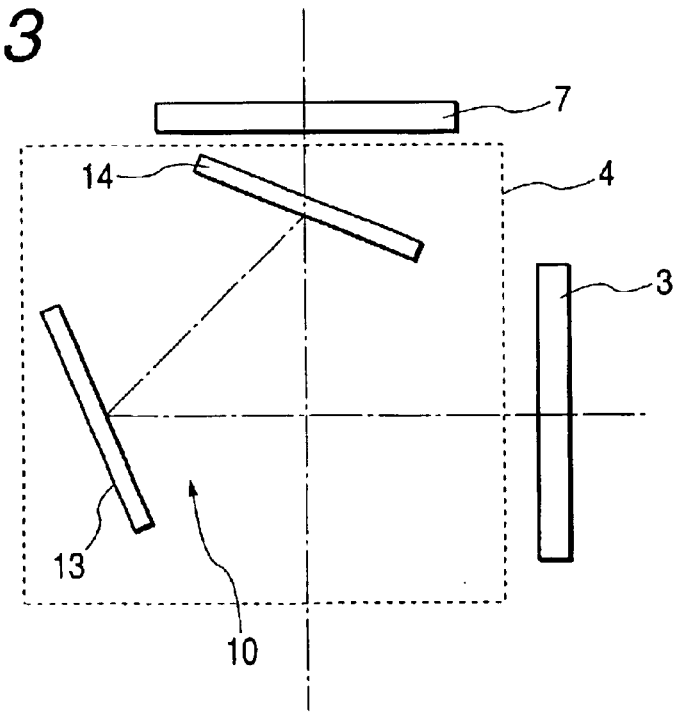
FIG. 3 is a diagram showing another third example of the light beam splitter to be used in the optical apparatus according to the present invention.

Usable as the optical element 10 of the light beam splitter 4 are a rectangular element which consists of two triangular prisms 11 and 12 which are cemented to each other as shown in FIG. 2, an element which consists of two plane parallel plates 13 and 14 each disposed at an inclination angle of 22.5° relative to an illuminating optical axis as shown in FIG. 3 and the like element.

Furthermore, a second optical filter 7a which is disposed in the second wavelength selecting member as the second wavelength selecting element is configured to have a predetermined wavelength characteristic and transmit only the fluorescent light out of the fluorescent light and reflected light.

Out of the fluorescent light and the reflected light which are incident on the second wavelength selecting member 7 which is configured as described above, only the fluorescent light transmit through the second optical filter 7a. The fluorescent light which has transmitted through the second wavelength selecting member 7 form a fluorescence image with the imaging lens 8 at a predetermined location on the detector 8. An eyepiece which is disposed in the vicinity of the location of the fluorescence image makes it possible to visually observe the fluorescence image. Since this fluorescence image is remarkably dark, it is preferable for picking up this image to dispose an electronic image pickup device such as a cooled CCD, an image pickup device having a high sensitivity in particular.

Now, description will be made of an optical element of the light beam splitter which is to be used in the optical apparatus according to the first embodiment of the present invention.

The optical element to be used in the first embodiment is, for example, a plane parallel plate which is shown in FIG. 1 and has a wavelength characteristic of transmittance not lower than 85% and reflectance not higher than 15% at least in a wavelength region not shorter than 400 nm and not longer than 700 nm.

Figure 4:
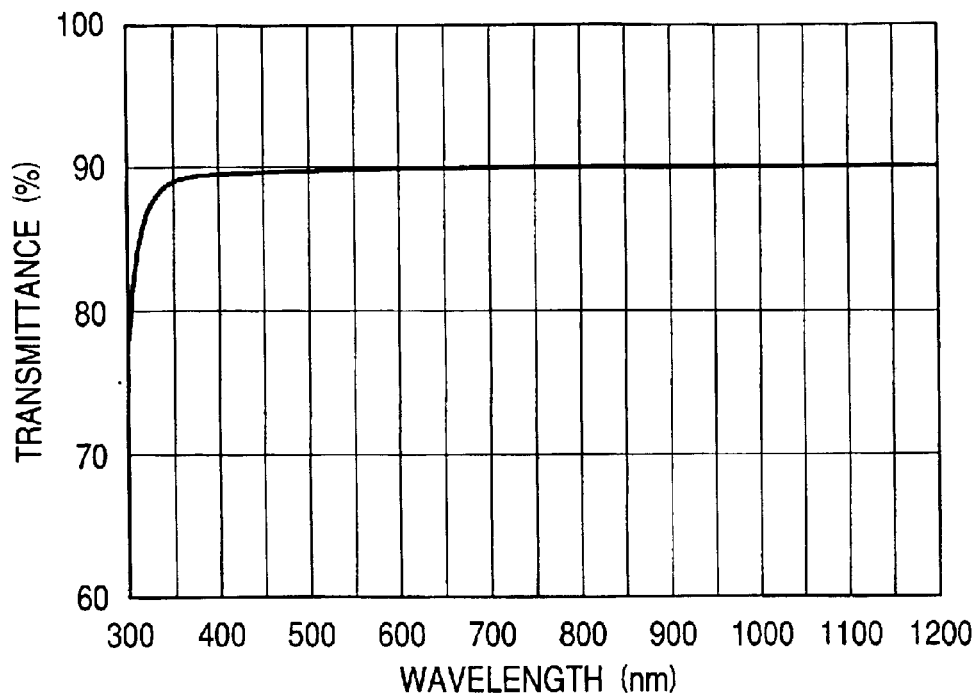
FIG. 4 is a diagram showing a spectral transmittance characteristic of an optical element of a light beam splitter to be used in the optical apparatus according to the first embodiment of the present invention.
Figure 5:
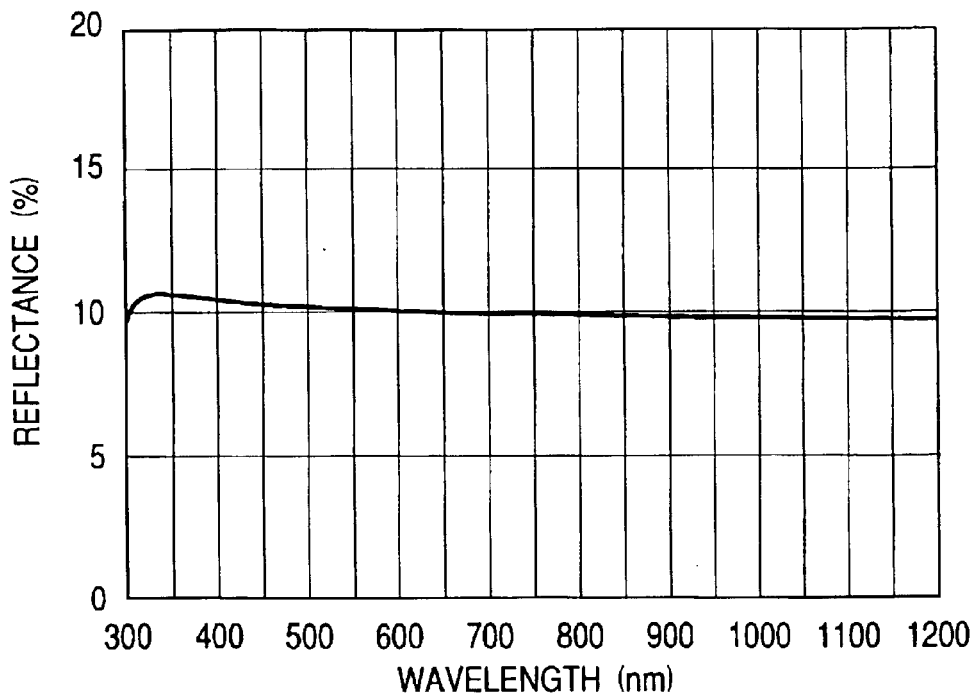
FIG. 5 is a diagram showing a spectral reflectance characteristic of the optical element shown in FIG. 4.

FIGS. 4 and 5 show an example of wavelength characteristic of the optical element to be used in the optical apparatus according to the first embodiment. Substrate glass S-BSL7 (prepared by Ohara, Co., Ltd., Japan) which has two polished surfaces is used with no modification as a material of the optical element. FIG. 4 shows a spectral transmittance characteristic of the optical element at wavelengths from 300 nm to 1200 nm and FIG. 5 shows a spectral reflectance characteristic of the same optical element at the wavelengths from 300 nm to 1200 nm.

Since the substrate glass S-BSL7 is used directly as the material of the optical element which is to be used in the first embodiment, that is, since this optical element is used with no coating, the optical element has resistance to deterioration with time lapse and physical impacts which is remarkably higher than that of a dichroic mirror for multiple excitation.

Since the optical apparatus according to the first embodiment uses the optical element of the light beam splitter which has reflectance nearly constant in the wavelength region from 400 nm to 1200 nm, this optical apparatus irradiates a sample with the excitation light after this light is reflected at the same reflectance at all wavelengths so far as the excitation light have wavelengths within this wavelength region. Accordingly, it is unnecessary for the optical apparatus to use a dichroic mirror for multiple excitation which is problematic in a durability or use a plurality of exclusive dichroic mirrors corresponding to fluorescent dyes in exchange so far as the first and second filters are selected appropriately and the optical apparatus is capable of remarkably lowering an intensity of the excitation light for irradiating samples without another optical element such as an ND filter, thereby lessening damages on the samples.

Description has been made above concretely of the optical element of the light beam splitter which is configured as shown in FIG. 1 out of light beam splitters to be used in the first embodiment, and it is sufficient also for light beam splitters which have configurations shown in FIGS. 2 and 3 to configure the light beam splitters so as to have transmittance not lower than 85% and reflectance not higher than 15% at least in a wavelength region not shorter than 400 nm and not longer than 700 nm as a while by selecting materials composing optical elements.

It is desirable that the optical element of the light beam splitter to be used in the optical apparatus according to the present invention satisfies the following condition (1):

$$n<2.0 \tag{1}$$

wherein a reference symbol represents a refractive index of the above described optical element.

Now, description will be made of an optical apparatus according to a second embodiment of the present invention.

Figure 6:
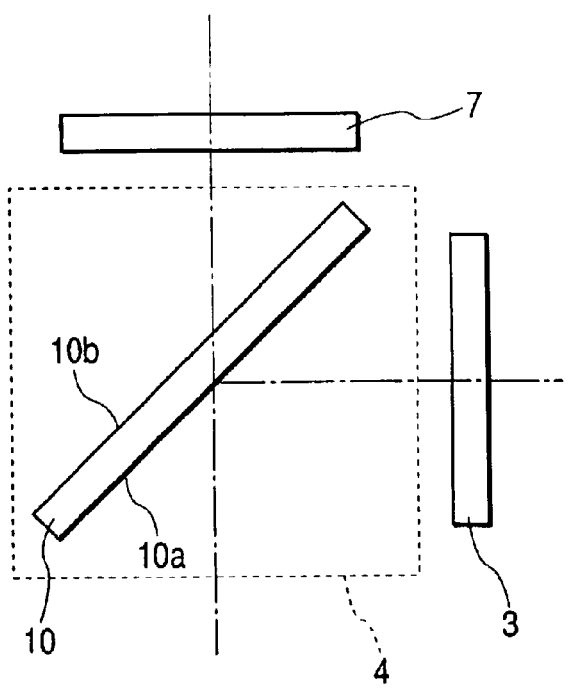
FIG. 6 is a diagram showing a configuration of a light beam splitter to be used in an optical apparatus according to a second embodiment of the present invention.

An overall configuration of the optical apparatus according to a second embodiment of the present invention is shown in FIG. 1 and substantially the same as that of the optical apparatus according to the first embodiment. However, a light beam splitter used in the optical apparatus according to the second embodiment is configured as shown in FIG. 6 and uses an optical element 10 having antireflection coatings on a surface 10a (first surface) on which excitation light is to be incident and an opposite surfaces (second surface) 10b.

The antireflection coatings on these surfaces 10a and 10b enhance transmittance of this optical element, thereby making it possible to lead fluorescent light with a high efficiency from a sample to a second wavelength selecting member and a detector, weaken excitation light for irradiating the sample and lessen a damage on the sample.

Figure 7:
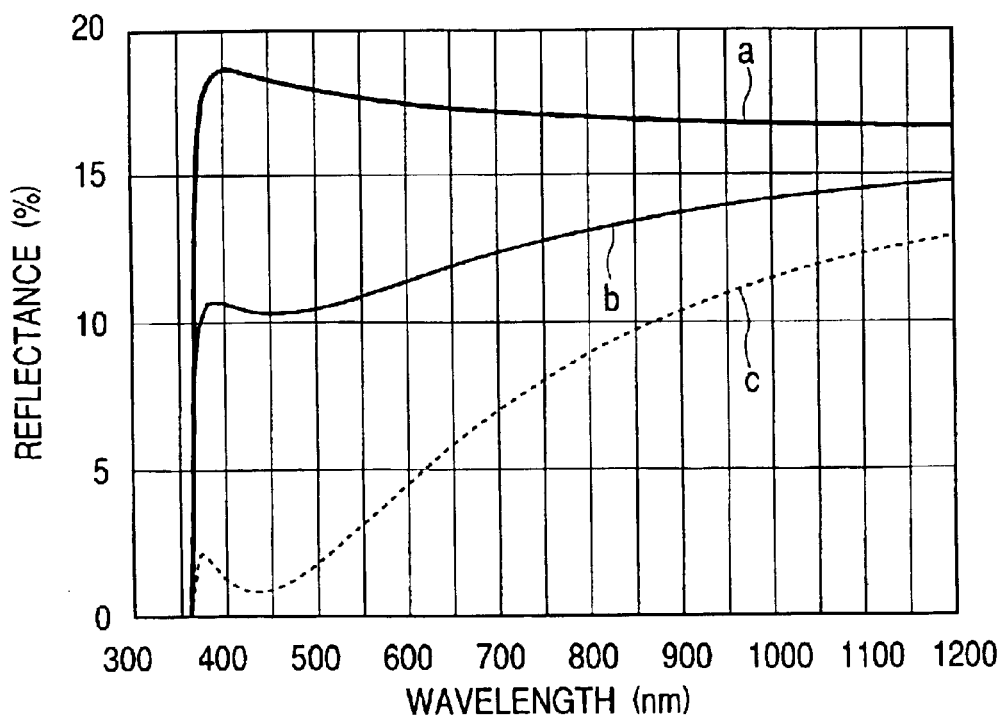
FIG. 7 is a diagram showing a spectral reflectance characteristic of as optical element which is to be used in the second embodiment of the present invention and uses substrate glass S-TIH6.
Figure 8:
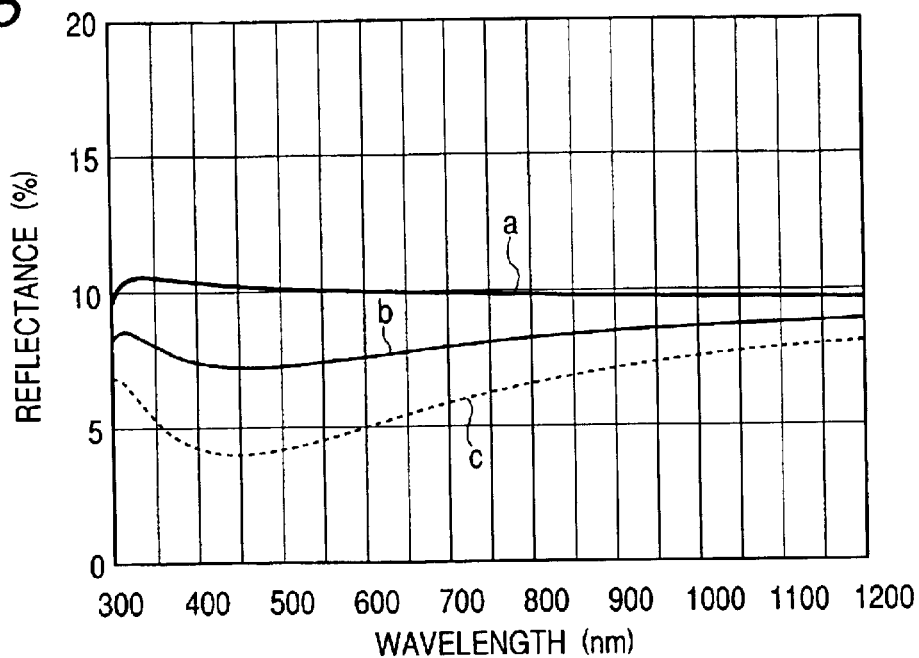
FIG. 8 is a diagram showing a spectral reflectance characteristic of an optical element which is to be used in the second embodiment of the present invention and uses substrate glass S-BSL7.
Figure 9:
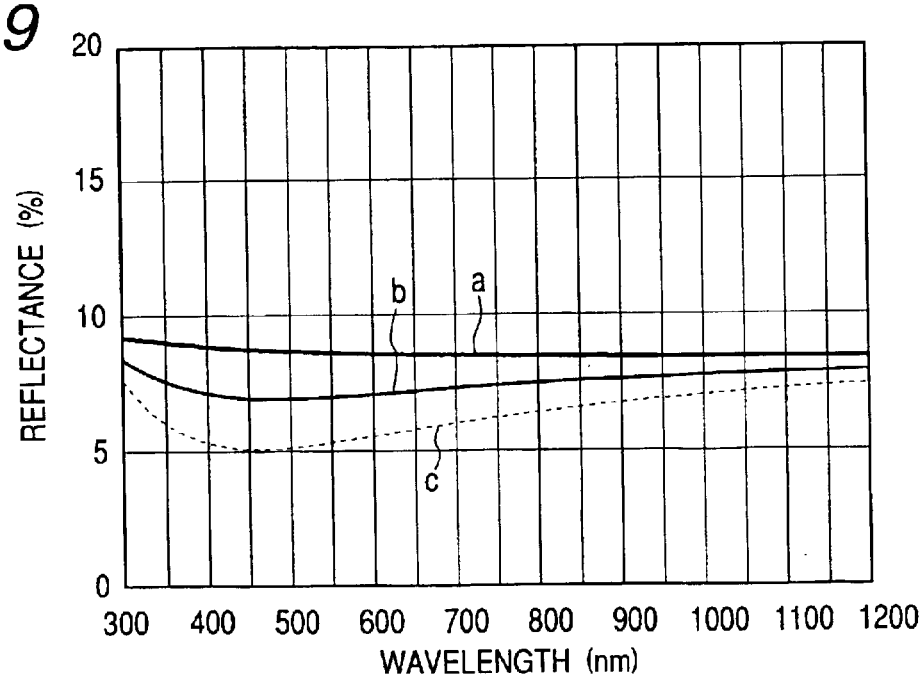
FIG. 9 is a diagram showing a spectral reflectance characteristic of an optical element which is to be used in the second embodiment of the present invention and uses substrate glass of a synthetic quartz.

FIGS. 7, 8 and 9 show reflectance characteristics of optical elements of a light beam splitter which are to be used in the optical apparatus according to the second embodiment and have substrate glasses S-TIH6, S-BSL7 (both prepared by Ohara Co., Ltd., Japan) and of a synthetic quartz respectively each 1 mm thick. In these drawings, a is a curve showing a reflectance characteristic in a case where the optical element has no antireflection coating, b is a curve showing a reflectance characteristic in a case where the optical element has an antireflection coating only on the second surface and c is a curve showing a reflectance characteristic in a case where the optical element has antireflection coatings on both the surfaces. Magnesium fluoride ($MgF_2$) is used as the antireflection coating in the second embodiment. However, a multi-layer coating may be used as the antireflection coating so far as the multi-layer coating is not problematic in deterioration with time and physical resistance.

Figure 10:
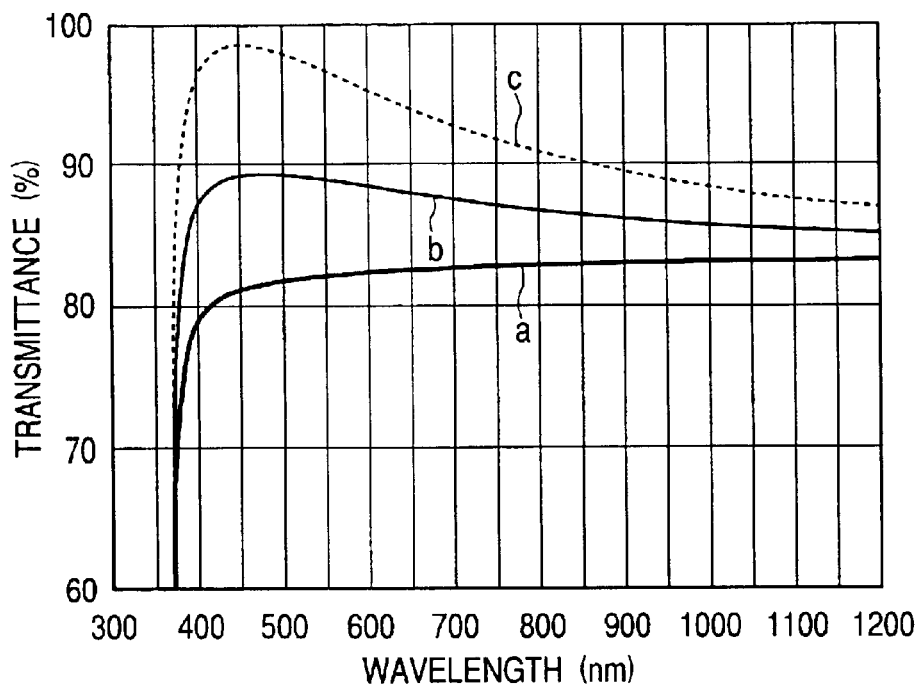
FIG. 10 is a diagram showing a spectral transmittance characteristic of an optical element which is to be used in the second embodiment of the present invention and uses substrate glass S-TIH6.
Figure 11:
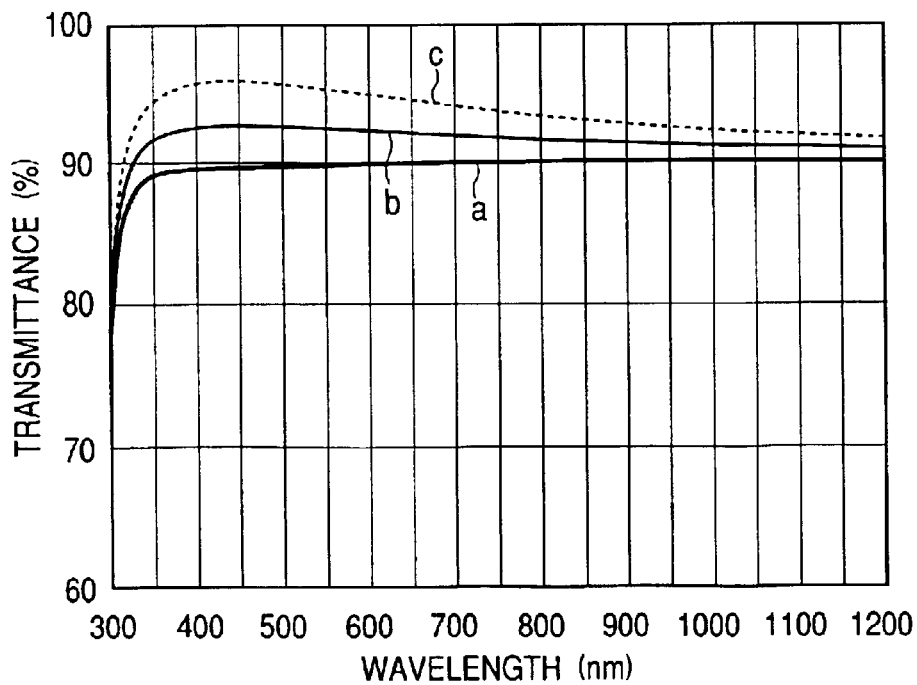
FIG. 11 is a diagram showing a spectral transmittance characteristic of an optical element which is to be used in the second embodiment of the present invention and uses substrate glass S-BSL7.
Figure 12:
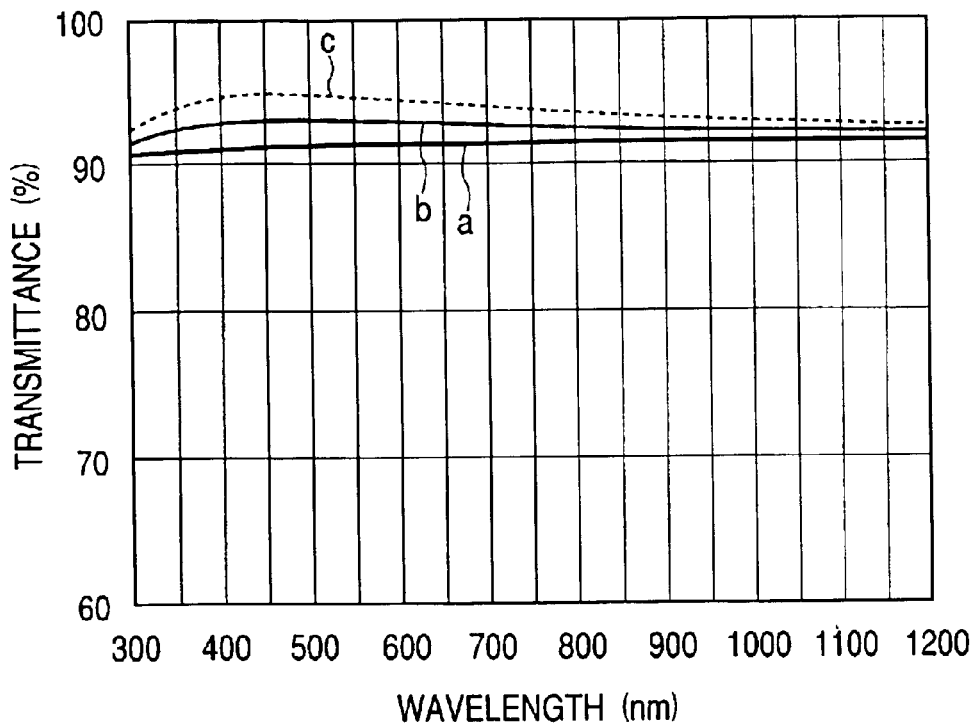
FIG. 12 is a diagram showing a spectral transmittance characteristic of an optical element which is to be used in the second embodiment of the present invention and uses substrate glass of synthetic quartz.

FIGS. 10, 11 and 12 show transmittance characteristics of the above described optical elements which have the substrate glasses S-TIH6, S-BSL7 (both prepared by Ohara Co., Ltd., Japan) and of the synthetic quartz respectively each 1 mm thick.

In these drawings, a is a curve showing a spectral transmittance characteristic in a case where the optical element has no antireflection coating, b is a curve showing a spectral transmittance characteristic in a case where the optical element has the antireflection coating only on the second surface and c is a curve showing a spectral transmittance characteristic in a case where the optical element has the antireflection coatings on both the surfaces.

As seen from FIGS. 7, 8, 9, 10, 11 and 12, it will be understood that an optical element which has transmittance of 85% and reflectance not higher than 15% at least in a wavelength region not shorter than 400 nm and not longer than 700 nm can be obtained using S-TIH6, S-BSL7 or the synthetic quartz as substrate glass of the optical element.

Since the optical element of the light beam splitter has the above described characteristics, almost all excitation light which is incident on the optical element transmits through the optical element and excitation light is reflected only at a low ratio by the optical element in the optical apparatus according to the second embodiment.

When the optical element which has the antireflection coatings of the synthetic quartz on both the surfaces, approximately 5% of the excitation light is reflected toward the objective lens. Accordingly, the excitation light transmits through the objective lens and reach a sample at a slight ratio. The optical apparatus according to the second embodiment therefore prevents the sample from being damaged and permits easily observing living cells. However, fluorescent light emitted from the sample has low intensities since the excitation light has remarkably low intensities. It is therefore preferable to use an electronic image pickup device as a detector.

An optical apparatus according to a third embodiment of the present invention has a configuration which is substantially the same as that of the optical apparatus according to the first or second embodiment shown in FIG. 1. However, the third embodiment is different from the first or second embodiment in that the optical elements used in the first or second embodiment are disposed switchably to a conventionally used dichroic mirror in the third embodiment.

Figure 13:
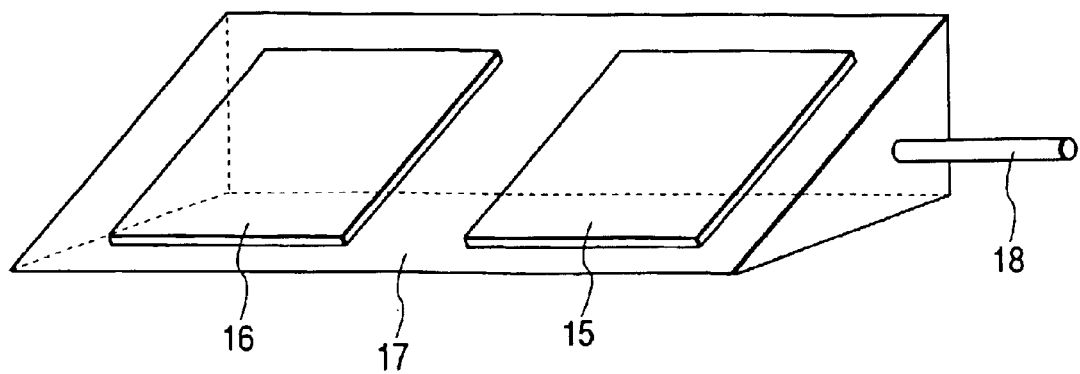
FIG. 13 is a diagram showing a configuration of a light beam splitter which is to be used in an optical apparatus according to a third embodiment of the present invention.

FIG. 13 shows a configuration of a light beam splitter to be used in the third embodiment in which an optical element 15 and a dichroic mirror 16 are held by a common holding member 17 so as to be set and removed into and out of an optical path with a lever 18.

Fluorescent light have remarkably low intensities as described above in an optical apparatus which uses a light beam splitter configured to set the optical element 15 in the optical path. The optical apparatus may therefore be inconvenient for observing a fluorescence image by eyes and positioning a sample.

The optical apparatus according to the third embodiment which uses the above described light beam splitter is capable of increasing an amount of excitation light to irradiate a sample by switching the optical element 15 to the dichroic mirror 6, thereby allowing a fluorescence image to be observed by eyes. Furthermore, the optical apparatus allows a sample to be positioned easily when an objective lens is set at a low magnification.

Even when an objective lens which has a high magnification and a large numerical aperture is used, the optical apparatus is capable of extremely increasing an amount of excitation light. Accordingly, the optical apparatus permits utilizing a method for investigating functions of specific proteins in cells, that is, a technique referred to as photobleaching, by intentionally fading colors of fluorescent dyes and then observing situations of fluorescent light which increase light intensities.

Figure 14:
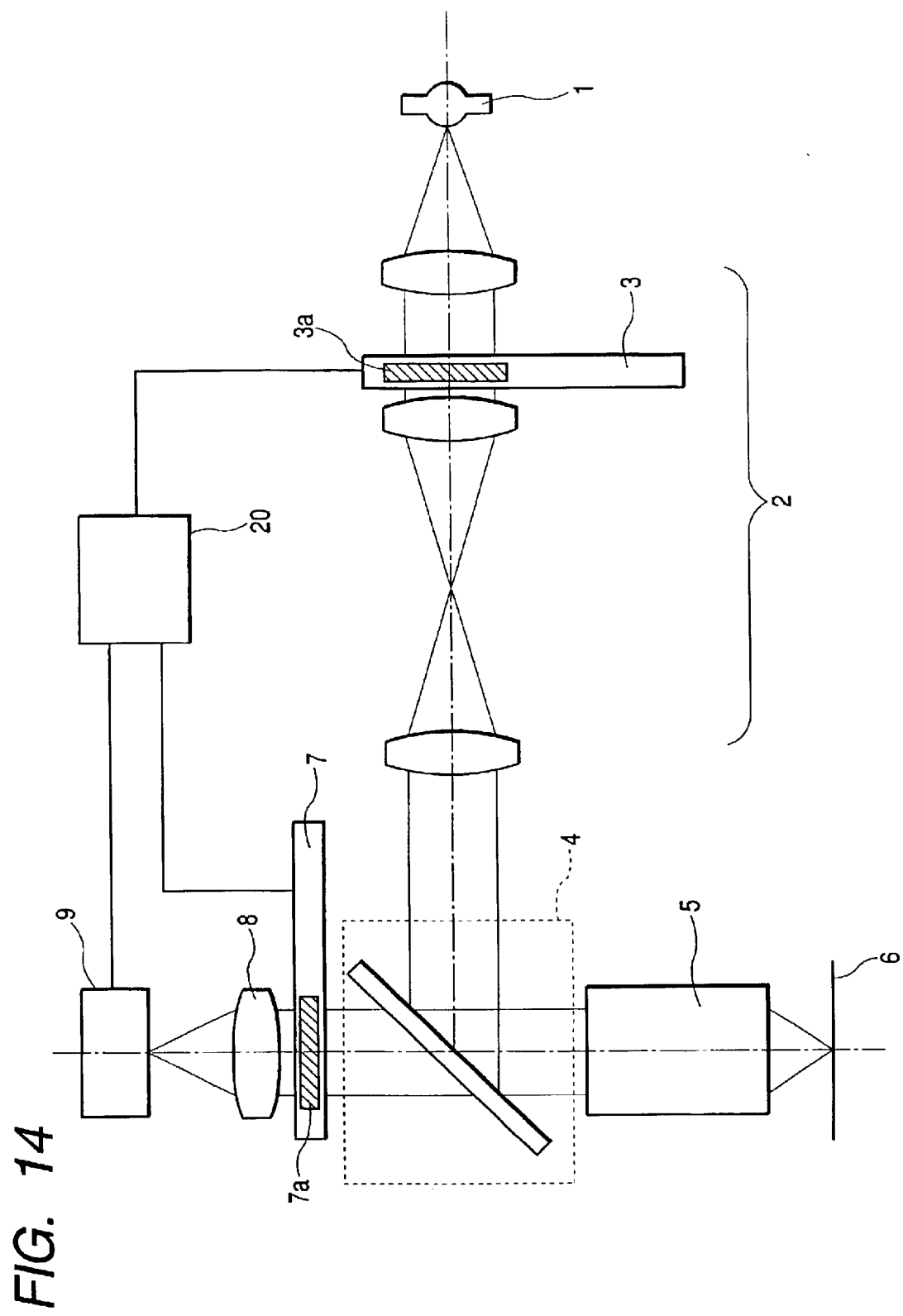
FIG. 14 is a diagram showing a configuration of an optical apparatus according to a fourth embodiment of the present invention.

Furthermore, a fourth embodiment of the present invention has a configuration shown in FIG. 14, in which a reference numeral 1 represents a light source, a reference numeral 2 designates an illuminating optical system, a reference numeral 3 denotes a first wavelength selecting member, a reference numeral 4 represents a light beam splitter, a reference numeral 5 designates an objective lens, a reference numeral 6 denotes a sample, a reference numeral 7 represents a second wavelength selecting member, a reference numeral 8 designates an imaging lens and a reference numeral 9 denotes a detector: these members being configured fundamentally the same as those shown in FIG. 1.

However, the fourth embodiment is different from the other embodiments in that each of the first wavelength selecting member and the second wavelength selecting member uses a plurality of wavelength selecting elements which have different optical characteristics and are controlled by a computer 20 in the fourth embodiment. An optical apparatus according to the fourth embodiment is configured to have a plurality of first filters having different optical characteristics and a plurality of second filters having different optical characteristics, and dispose a combination of the first optical filter and the second optical filter most suited to a desired fluorescent dye in an optical path with the computer 20.

Figure 15:
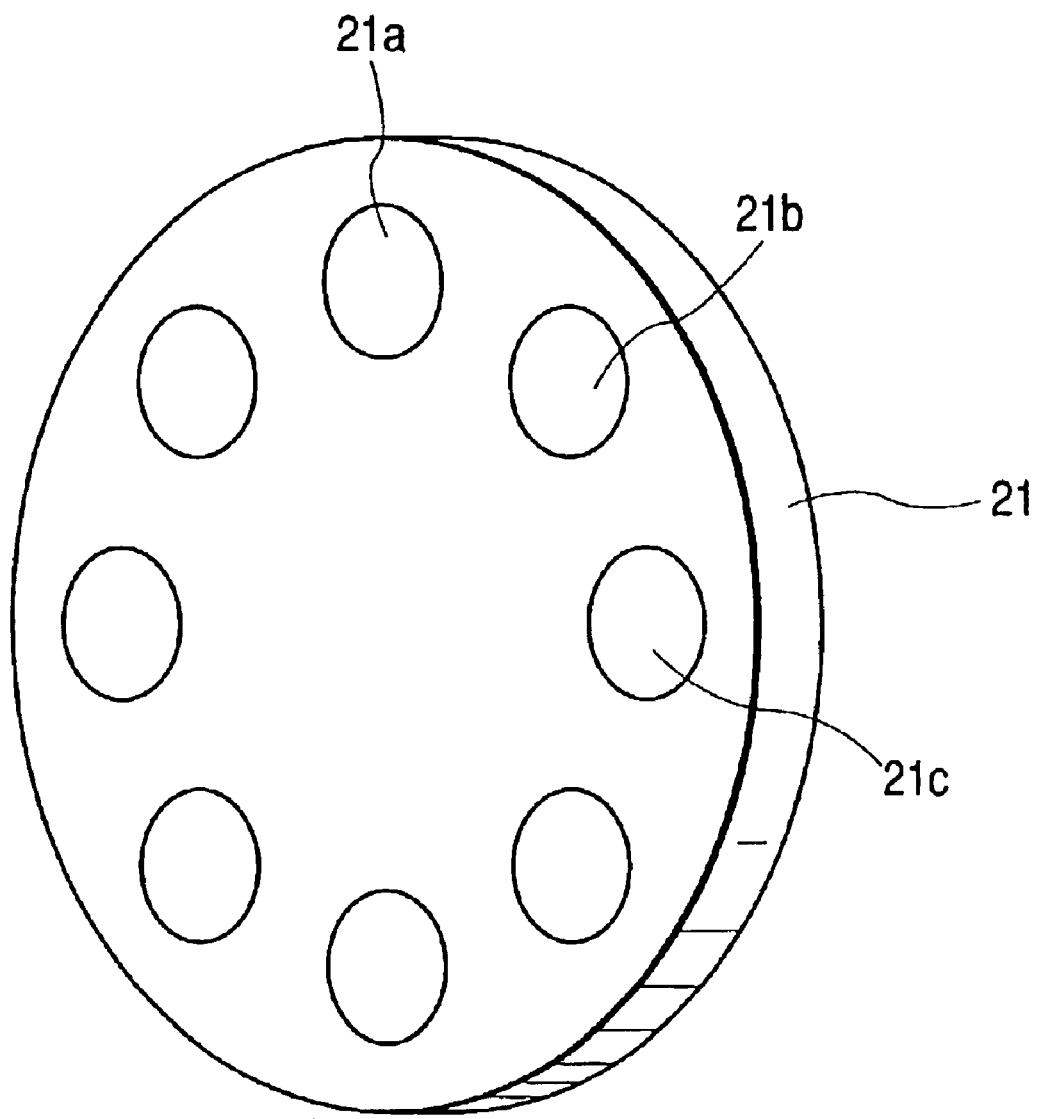
FIG. 15 is a diagram showing a configuration of first and second wavelength selecting members in the fourth embodiment of the present invention.

FIG. 15 shows configurations of the first and second wavelength selecting members used in the fourth embodiment. The wavelength selecting member is configured to dispose a plurality of optical filters 21a, 21b . . . corresponding to fluorescent dyes in a turret like filter wheel 21 which is electrically rotatable as shown in FIG. 15 and allow an optional optical filter to be set and removed into and out of an illuminating optical path or an imaging optical path under computer control. The optical filters used in the fourth embodiment are excitation filters for multiple excitation and absorption filters shown in the drawing or excitation filters each corresponding to a single fluorescent dye and absorption filters shown in the drawing.

Figure 16:
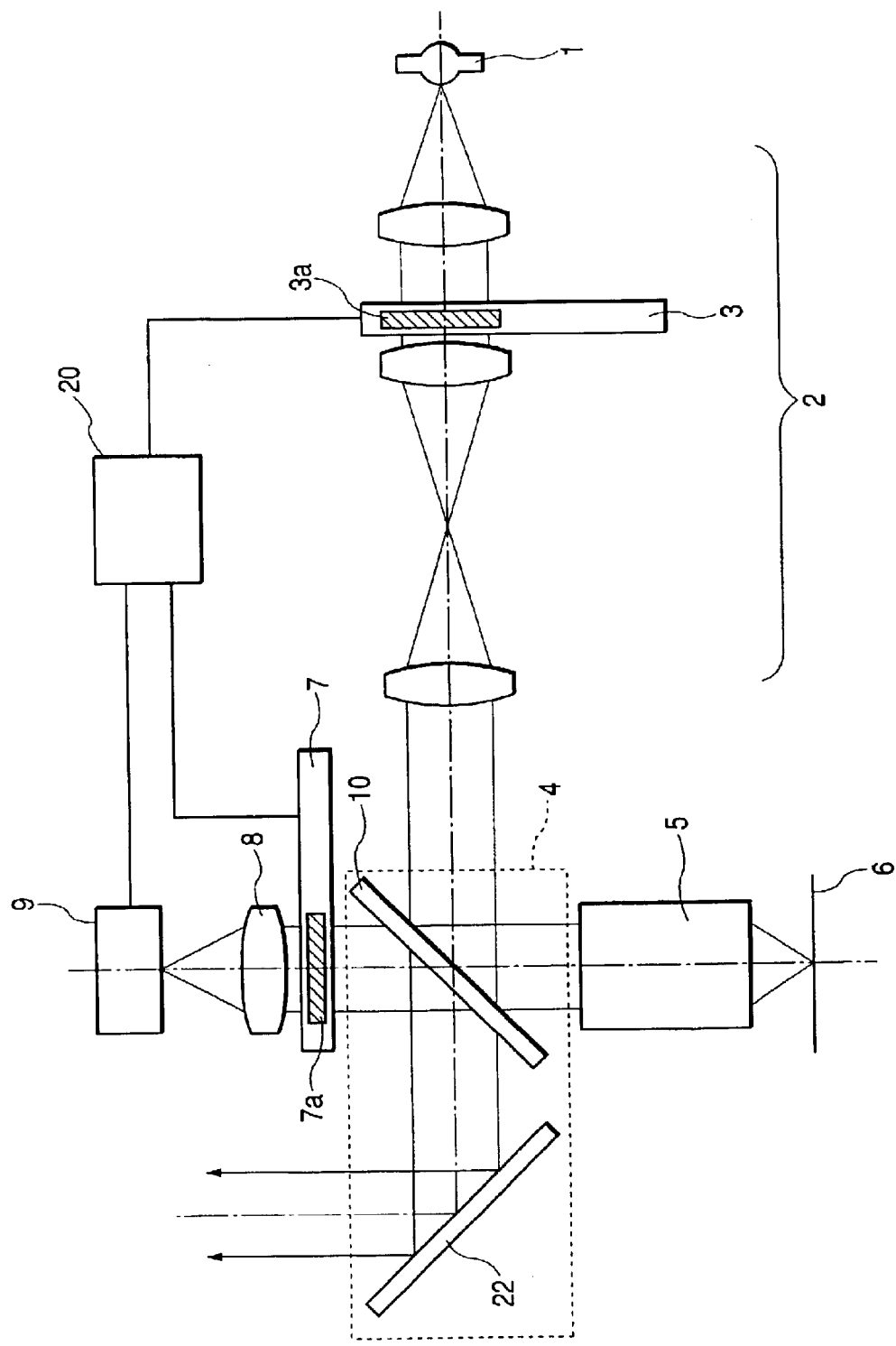
FIG. 16 is a diagram showing a modification example of the optical apparatus according to the fourth embodiment of the present invention.

Furthermore, FIG. 16 shows a modified example of the fourth embodiment of the present invention, in which a mirror 22 is added to the light beam splitter. Excitation light incident from a light source onto the light beam splitter is reflected by an optical element 10 in the light beam splitter 4 toward a sample 6, but a portion of the excitation light transmits through the optical element. It is not preferable to allow the light which has transmitted through the optical element 10 to be returned to the optical element due to reflection on an inside surface of a microscope tube and incident on an observing optical path. In order to prevent the light from being returned to the optical element, the above described mirror 22 functions to lead the excitation light which has transmitted through the optical element outside the observing optical path. It is therefore preferable to determine a location and an inclination angle of the mirror 22 so that the light reflected by the optical element is not returned to the optical element.

Means for leading the unwanted excitation light outside which is shown in FIG. 16 (a light trap mechanism) is applicable also to the first, second and third embodiments.

Figure 20A:
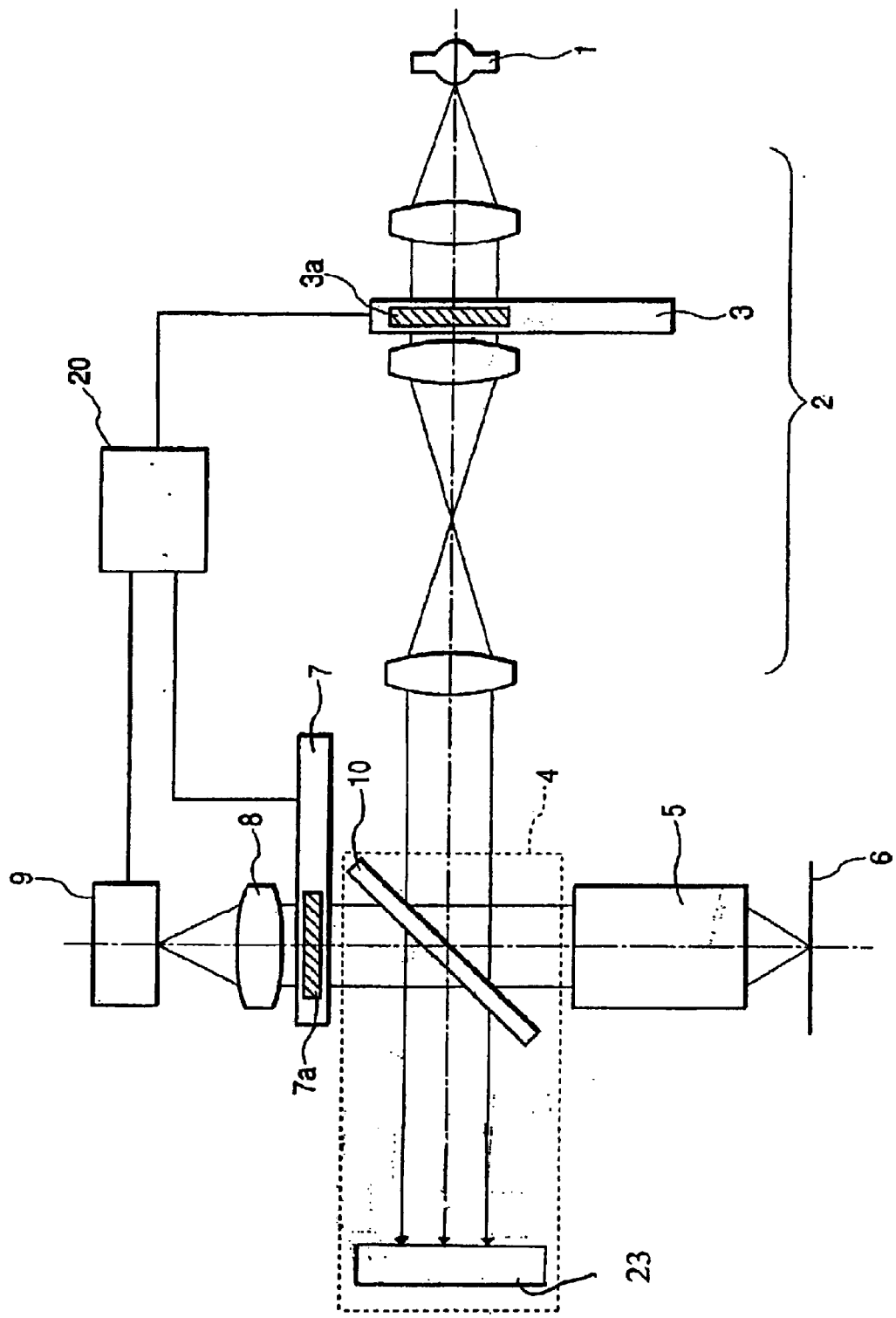
FIG. 20A and FIG. 20B are diagrams showing configurations of an optical apparatus according to the present invention with a light trap.
Figure 20B:
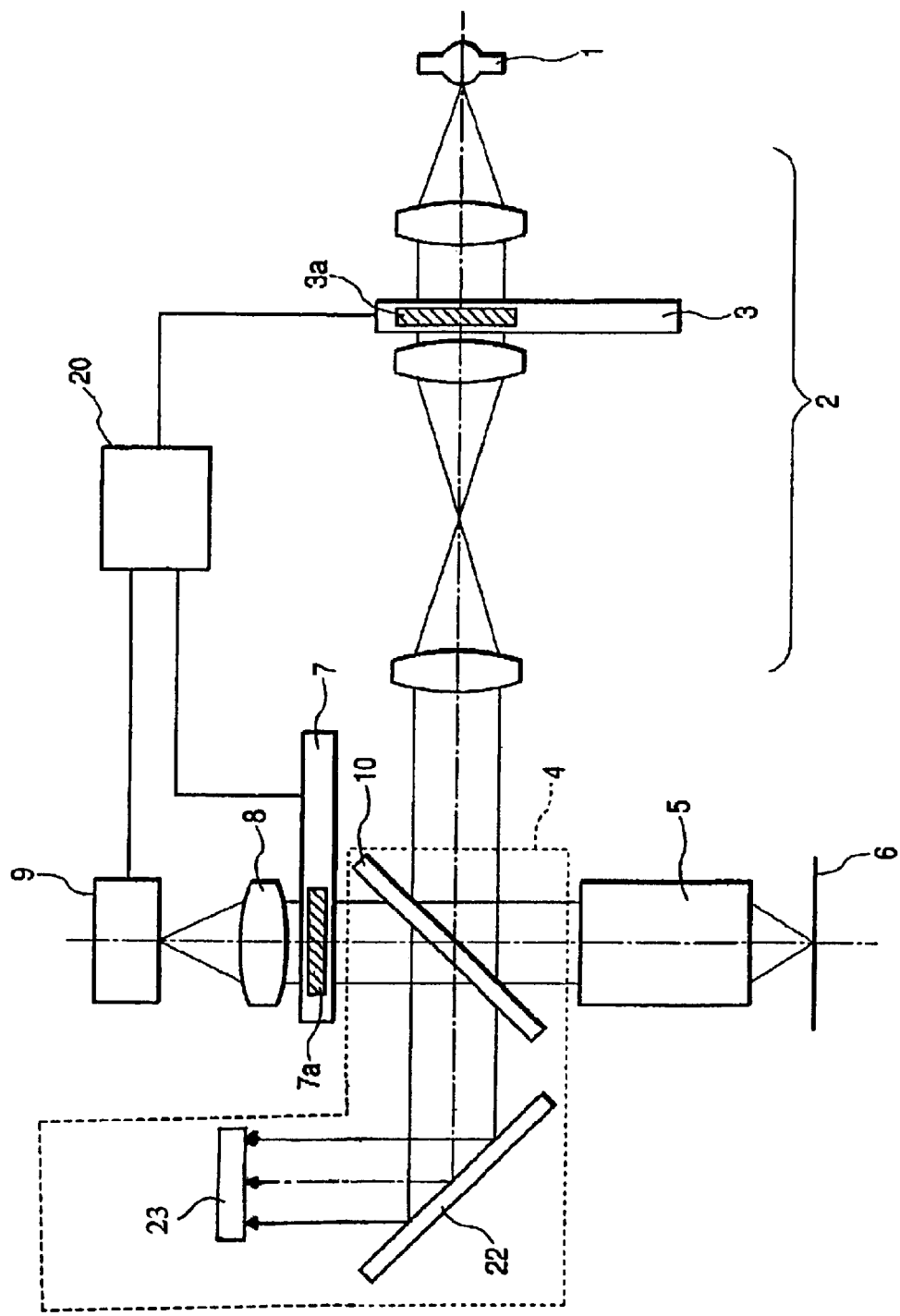

Light which has been emitted from a light source and transmitted through an optical element of a light beam splitter may be eliminated with an absorption filter or a light absorbing member 23 which is disposed as a light trap mechanism at an appropriate location in place of a mechanism configured to reflect the light with a mirror 22 as shown in FIG. 20A. Alternatively, a light absorbing member 23 may absorb light reflected from mirror 22, as shown in FIG. 20B. This light trap mechanism utilizing absorption is applicable also to the other embodiments.

Figure 17A:
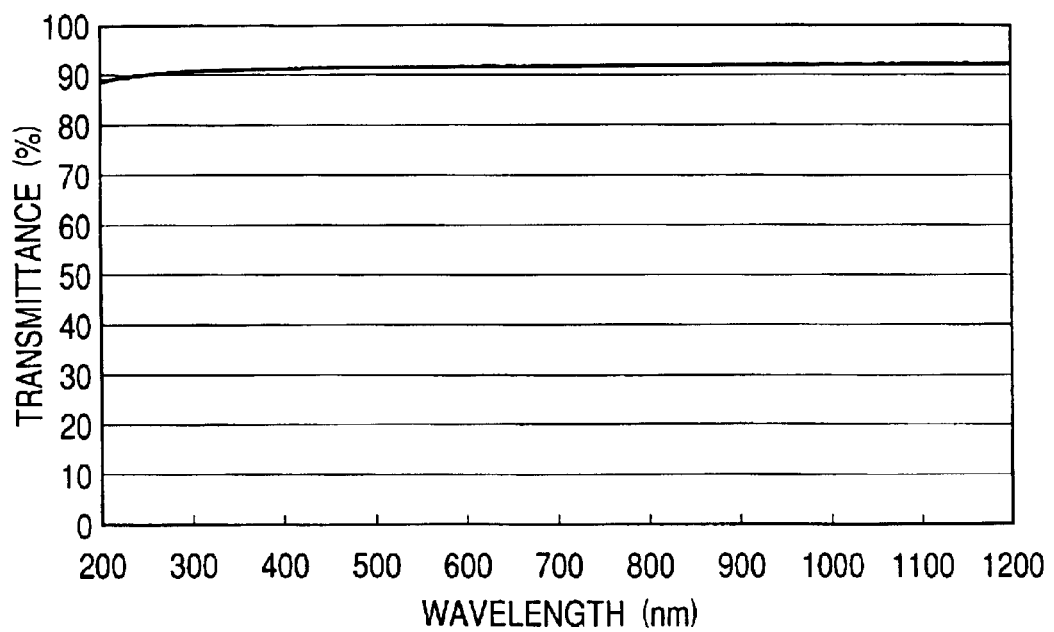
FIG. 17A and FIG. 17B are diagrams showing a spectral transmission characteristic and a reflection characteristic of quartz having an antireflection coating.
Figure 17B:
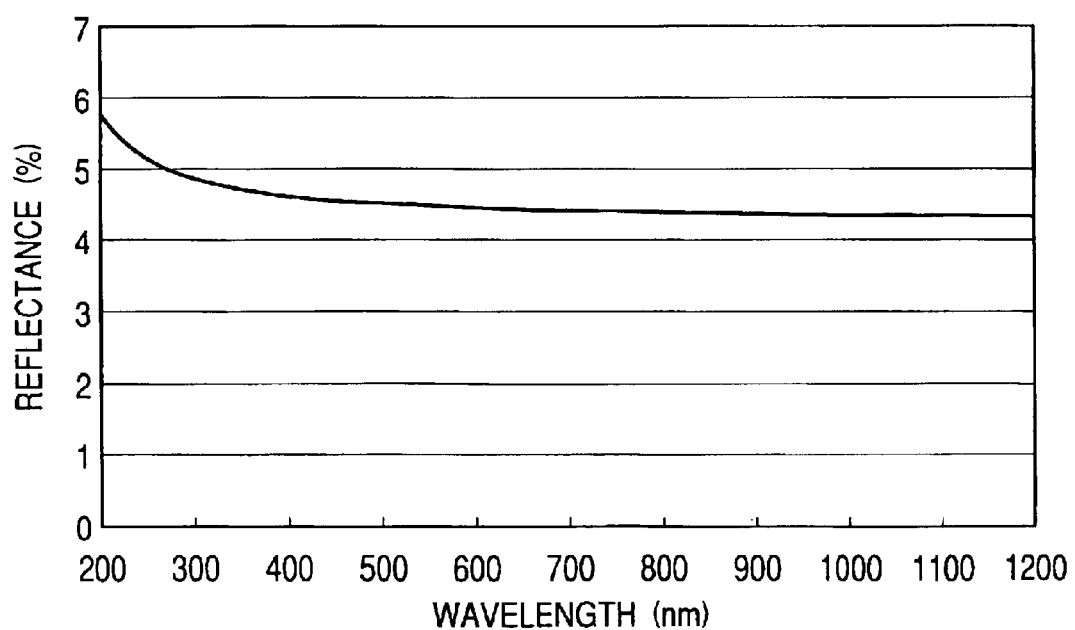

In addition, quartz which has an antireflection coating may be used as the optical element 10. In this case, a transmission and reflection characteristics of transmittance not lower than 85% and reflectance not higher than 10% in a wavelength region not shorter than 200 nm and not longer than 1000 nm are obtained as shown in FIG. 17A and FIG. 17B.

Figure 18A:
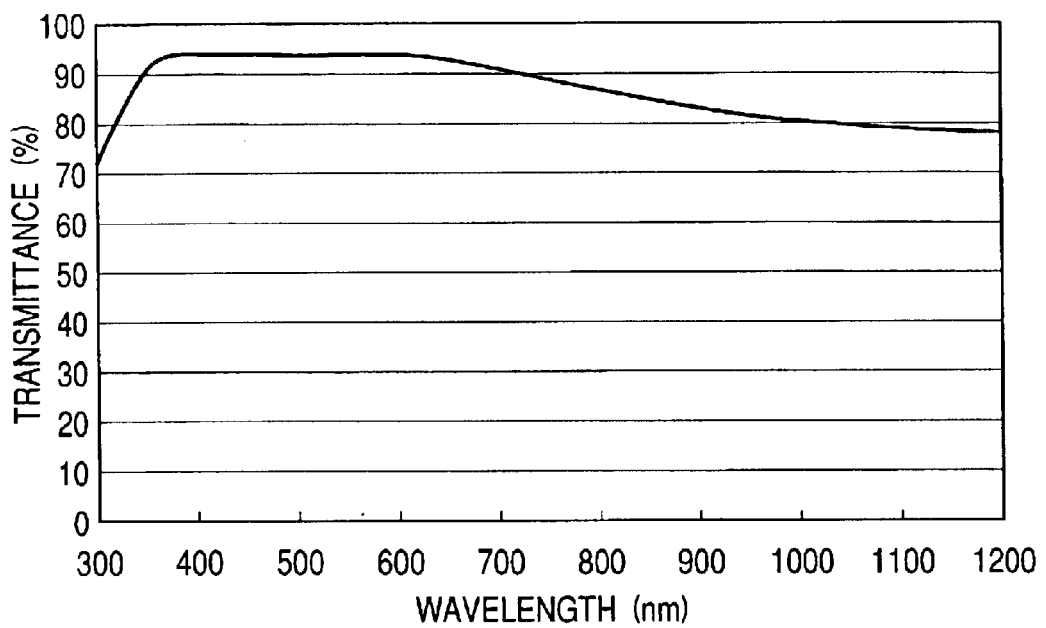
FIG. 18A and FIG. 18B are diagrams showing a spectral transmission characteristic and a refection characteristic of substrate glass S-BSL7 having multiple coatings.
Figure 18B:
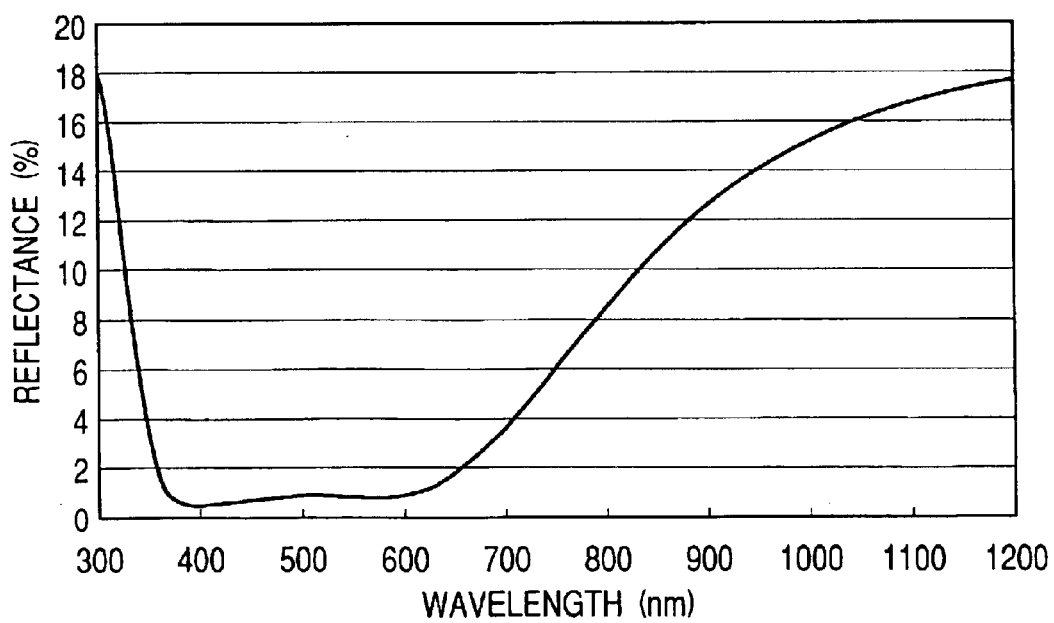
Figure 19:
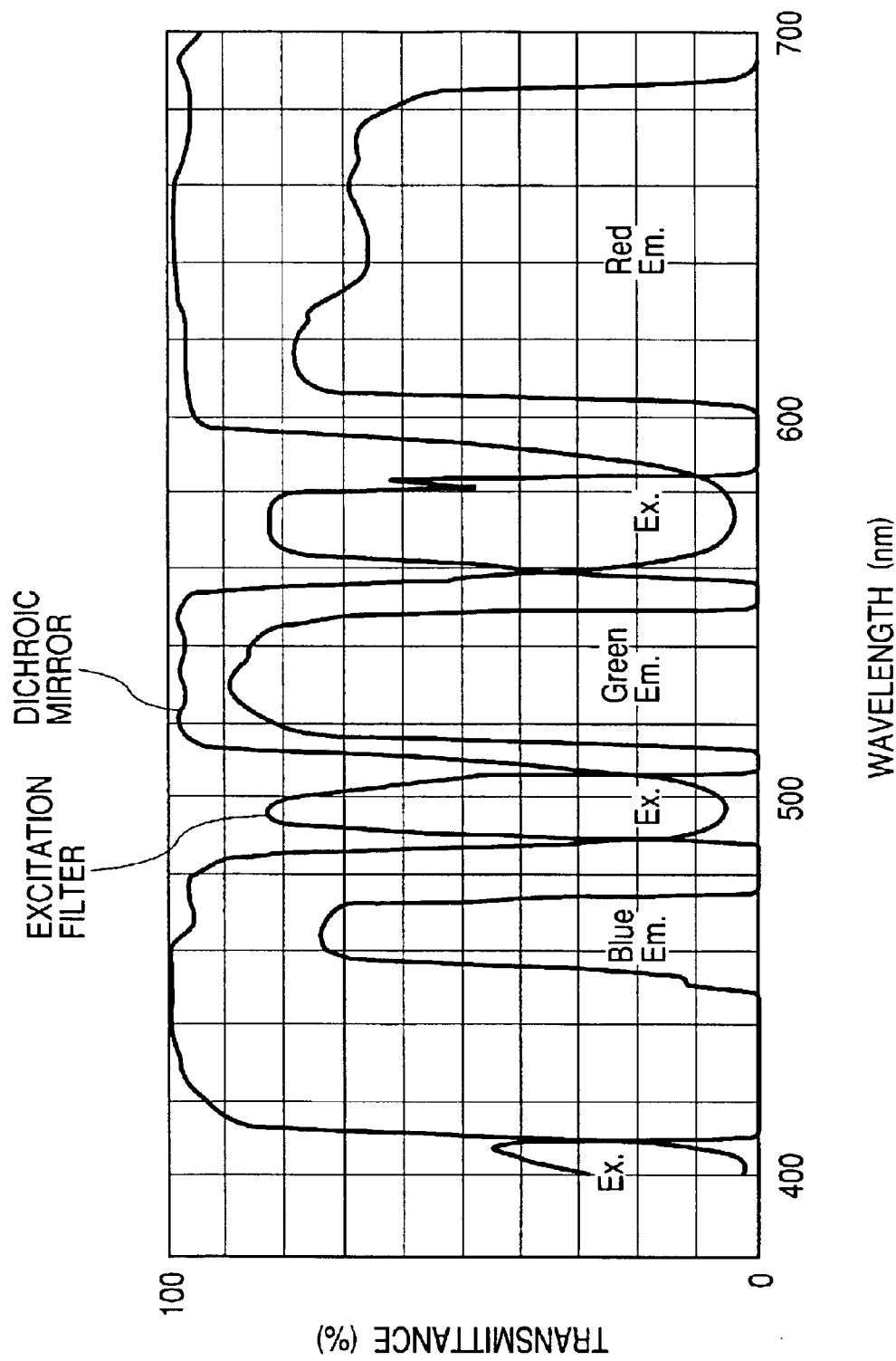
FIG. 19 is a diagram showing a spectral transmittance characteristic of a dichroic mirror for multiple excitation.

Furthermore, S-BSL7 may have multiple coatings as the antireflection coatings. In this case, a transmission and reflection characteristics of transmittance not lower than 90% and reflectance not higher than 5% in a wavelength region not shorter than 400 nm and not longer than 700 nm can be obtained as shown in FIG. 18A and FIG. 18B.

The optical apparatus according to the present invention makes it possible to simultaneously observe samples which are dyed quadruply, quintuply or more multiply with fluorescent dyes and permits fluorescence observation optimum for functional analyzes of living cells.

What is claimed is:

1. An optical apparatus comprising:
   a light source;
   an illuminating optical system for illuminating a sample with illuminating light emitted from said light source;
   a first wavelength selecting member;
   a light beam splitter for leading said illuminating light to the sample an objective lens disposed between said light beam splitter and said sample;
   a detector for detecting light from the sample through the objective lens; and
   a second wavelength selecting member disposed between said objective lens and said detector, wherein said first wavelength selecting member has at least a wavelength selecting element which selectively transmits light having wavelengths in a predetermined region out of said illuminating light, wherein said second wavelength selecting member has at least a wavelength selecting element which selectively transmits light having a predetermined wavelength out of light reflected or emitted from said sample, wherein said light beam splitter has an optical element, and wherein said optical element has a transmittance characteristic not lower than 85% and a reflectance characteristic not higher than 15% at least in a wavelength region not shorter than 400 nm and not longer than 700 nm.

2. The optical apparatus according to claim 1, wherein said optical element has a first surface and a second surface in order from a side of incidence of said illuminating light, and wherein said second surface has a antireflection coating or said first and second surfaces have antireflection coatings.

3. The optical apparatus according to claim 1, wherein said light beam splitter has a dichroic mirror, and wherein said optical element and said dichroic mirror are switchable.

4. The optical apparatus according to claim 1, wherein the optical element of said light beam splitter satisfies the following condition (1):
   (1) n<2.0 wherein a reference symbol n represents a refractive index of the optical element for the d-line.

5. The optical apparatus according to claim 1, wherein the optical element of said light beam splitter has an antireflection coating on a surface opposite to a surface on which the illuminating light are incident.

6. The optical apparatus according to claim 3, wherein said light beam splitter has a unit comprising said wavelength selecting element for selectively transmitting light having wavelengths in a predetermined region out of the illuminating light, said dichroic mirror and said wavelength selecting element for selectively transmitting light having wavelengths in a predetermined region out of light reflected and emitted from the sample illuminated with the illuminating light which are integrally held, and wherein said optical element and said unit are switchably configured.

7. The optical apparatus according to claim 1, wherein said light beam splitter has a light trap mechanism on a side of said optical element through which the illuminating light transmits.

8. The optical apparatus according to claim 1, wherein said first wavelength selecting member has a plurality of wavelength selecting elements and a first selecting mechanism which selects a wavelength selecting element out of said wavelength selecting elements.

9. The optical apparatus according to claim 1, wherein said second wavelength selecting member has a plurality of wavelength selecting elements and a second selecting mechanism which selects a wavelength selecting element out of said wavelength selecting elements.

10. The optical apparatus according to claim 1, wherein said detector is an electronic image pickup device.

11. The optical apparatus according to claim 10, wherein said electronic image pickup device is a high sensitivity image pickup device.

12. The optical apparatus according to claim 11 further comprising a computer and configured to control the first wavelength selecting member and the second wavelength selecting member with the computer.

13. The optical apparatus according to claim 12, wherein said high sensitivity image pickup device is controlled by said computer.

14. The optical apparatus according to claim 1, wherein said optical element has a first surface and a second surface in order from a side on which the illuminating light are incident, and wherein the first surface has an antireflection coating.

15. The optical apparatus according to claim 7, wherein said light trap mechanism has at least a reflecting surface.

16. The optical apparatus according to claim 15 wherein said reflecting surface is disposed so as to reflect incident light at an angle not smaller than 90 degrees.

17. The optical apparatus according to claim 15, said light trap mechanism has a plurality of reflecting surfaces, and is disposed in a plurality of wavelengths.

18. The optical apparatus according to claim 15, wherein said light trap mechanism has an absorbing member which absorbs incident light.

19. The optical apparatus according to claim 2, wherein said light beam splitter has a dichroic mirror, and wherein said optical element and said dichroic mirror are switchable.

20. The optical apparatus according to claim 2, wherein said light beam splitter has a unit comprising said wavelength selecting element for selectively transmitting light having wavelengths in a predetermined region out of the illuminating light, said dichroic minor and said wavelength selective element for selectively transmitting light having wavelengths in a predetermined region out of light reflected and emitted from the sample illuminated with the illuminating light which are integrally held, and wherein said optical element and said unit are switchably configured.

21. An optical apparatus comprising:
   a light source;
   an illuminating optical system for illuminating a sample with illuminating light emitted from said light source;
   a first wavelength selecting member;
   a light beam splitter for leading said illuminating light to the sample an objective lens disposed between said light beam splitter and said sample;
   a detector for detecting light from the sample through the objective lens; and
   a second wavelength selecting member disposed between said objective lens and said detector, wherein said first wavelength selecting member has at least a wavelength selecting element which selectively transmits light having wavelengths in a predetermined region out of said illuminating light, wherein said second wavelength selecting member has at least a wavelength selecting element which selectively transmits light having a predetermined wavelength out of light reflected or emitted from said sample, and wherein the optical element of said light beam splitter has a transmittance characteristic not lower than 85% and a reflectance characteristic not higher than 15% in a wavelength region not shorter than 330 nm and not longer than 1000 nm.

22. An optical apparatus comprising:

a light source;

an illuminating optical system for illuminating a sample with illuminating light emitted from said light source;

a first wavelength selecting member;

a light beam splitter for leading said illuminating light to the sample an objective lens disposed between said light beam splitter and said sample;

a detector for detecting light from the sample through the objective lens; and a second wavelength selecting member disposed between said objective lens and said detector, wherein said first wavelength selecting member has at least a wavelength selecting element which selectively transmits light having wavelengths in a predetermined region out of said illuminating light, wherein said second wavelength selecting member has at least a wavelength selecting element which selectively transmits light having a predetermined wavelength out of light reflected or emitted from said sample, and wherein the optical element of said light beam splitter has a transmittance characteristic not lower than 90% and a reflectance characteristic not higher than 5% in a wavelength region not shorter than 400 nm and not longer than 700 nm.

23. An optical apparatus comprising:

a light source;

an illuminating optical system for illuminating a sample with illuminating light emitted from said light source;

a first wavelength selecting member;

a light beam splitter for leading said illuminating light to the sample an objective lens disposed between said light beam splitter and said sample;

a detector for detecting light from the sample through the objective lens; and a second wavelength selecting member disposed between said objective lens and said detector, wherein said first wavelength selecting member has at least a wavelength selecting element which selectively transmits light having wavelengths in a predetermined region out of said illuminating light, wherein said second wavelength selecting member has at least a wavelength selecting element which selectively transmits light having a predetermined wavelength out of light reflected or emitted from said sample, and wherein the optical element of said light beam splitter has a transmittance characteristic not lower than 85% and a reflectance transmittance not higher than 10% in a wavelength region not shorter than 200 nm and not longer than 1000 nm.

* * * * *